US008311608B2

(12) United States Patent
Werner et al.

(10) Patent No.: US 8,311,608 B2

(45) Date of Patent: Nov. 13, 2012

(54) CONTINUOUS VESSEL-SELECTIVE SPIN LABELING

(75) Inventors: Richard Werner, Hamburg (DE); David G. Norris, Malden (NL)

(73) Assignee: Universitaetsklinikum Schleswig-Holstein, Kiel (DE)

( * ) Notice: Subject to any disclaimer, the term of this patent is extended or adjusted under 35 U.S.C. 154(b) by 1604 days.

(21) Appl. No.: 11/666,011

(22) PCT Filed: Oct. 21, 2005

(86) PCT No.: PCT/DE2005/001891

§ 371 (c)(1), (2), (4) Date: Apr. 23, 2007

(87) PCT Pub. No.: WO2006/042536

PCT Pub. Date: Apr. 27, 2006

(65) Prior Publication Data

US 2008/0089841 A1 Apr. 17, 2008

(30) Foreign Application Priority Data

Oct. 23, 2004 (DE) ......................... 10 2004 051 763

(51) Int. Cl.
*A61B 5/05* (2006.01)

(52) U.S. Cl. ......................... 600/410; 324/309; 324/310

(58) Field of Classification Search .................. 600/410; 324/309, 310

See application file for complete search history.

(56) References Cited

U.S. PATENT DOCUMENTS 5,402,785 A 4/1995 Leigh et al.
6,717,405 B2 4/2004 Alsop
2003/0193334 A1* 10/2003 Alsop .......................... 324/306

FOREIGN PATENT DOCUMENTS

WO WO 90/12329 10/1990

OTHER PUBLICATIONS

Werner et al., "Continuous Artery-Selective Spin Labeling (CASSL)", Magnetic Resonance in Medicine, vol. 53, pp. 1006-1012, Apr. 2005.

Eastwood et al., "Magnetic Resonance Imaging With Lateralized Arterial Spin Labeling", Magnetic Resonance Imaging, vol. 20, pp. 583-586, 2002.

Zaharchuk et al., "Multislice Perfusion and Perfusion Territory Imaging in Humans With Separate Label and Image Coils", Magnetic Resonance in Medicine, vol. 41, No. 6, pp. 1093-1098, Jun. 1999.

Hinshaw, "Image Formation by Nuclear Magnetic Resonance: The Sensitive-Point Method", Journal of Applied Physics, vol. 47, No. 8, pp. 3709-3721, Aug. 1976.

* cited by examiner

*Primary Examiner* — James Kish
*Assistant Examiner* — Saurel J Selkin
(74) *Attorney, Agent, or Firm* — Diederiks & Whitelaw, PLC

(57) ABSTRACT

The invention relates to a method for the MRT representation of a blood vessel (A) and/or of the territory supplied by the blood vessel (A) by labeling the blood, which is guided by this blood vessel (A), by means of continuous arterial spin labeling (CASL), in a specified labeling plane (E). The position of the labeling plan (E) is varied with the provision that a specified location of the blood vessel (A) remains in the labeling plane (E). This enables, for example, a selective labeling of a blood vessel of interest to be saturated by varying the position of the labeling plane.

19 Claims, 3 Drawing Sheets

Figure 1:
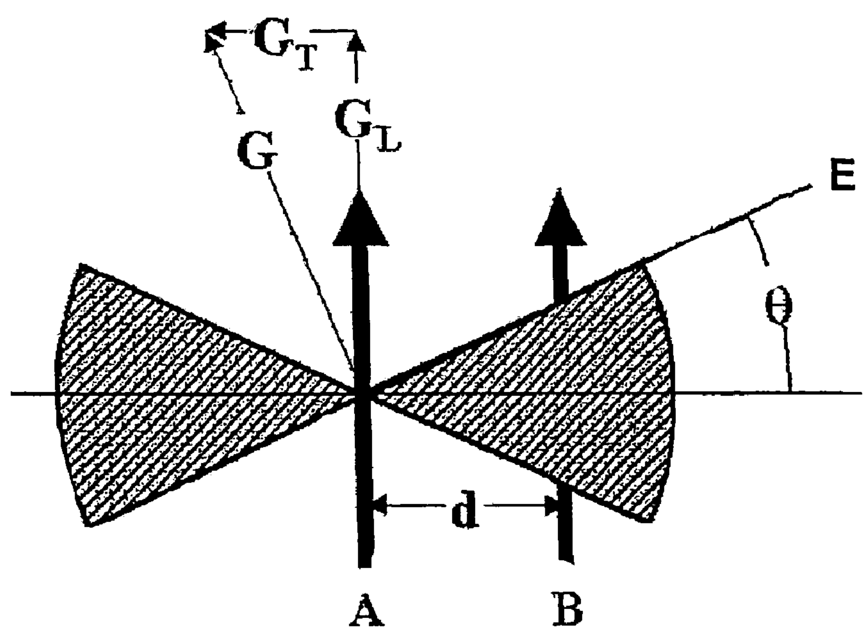

$G_T$
G
$G_L$
E
θ
d
A
B

CONTINUOUS VESSEL-SELECTIVE SPIN LABELING

CROSS-REFERENCE TO RELATED APPLICATIONS

This application represents a National Stage application of PCT/DE2005/001891 entitled "Continuous Vessel-Selective Spin Labeling" filed Oct. 21, 2005.

The invention relates to a method for the MRT representation of a blood vessel and/or the territory supplied by the blood vessel by labelling the blood guided by the blood vessel by means of continuous arterial spin labelling (CASL) in a specific labelling plane.

A number of methods have already been developed for the representation of a blood vessel and/or the territory supplied by the blood vessel and make it possible to obtain information on the arterial blood and oxygen supply of territories supplied by the blood vessel. These methods are more particularly of interest in the representation of cerebral perfusion territories, because the individual blood flow situation of the brain as a central neuroradiological question can differ as a result of a number of factors from the normal situation known on the basis of histological findings. Hereinafter reference is made in exemplified manner to the application of such methods in neuroradiology.

A widely used method in clinical practice is digital subtraction angiography (DSA). Through the injection of a contrast medium the vascular trees of the large artery supplying the brain are visualized and by advancing a catheter it is also possible to image the vascular trees of smaller arteries. The disadvantage of this method is that it is invasive and its implementation can represent a high risk particularly with patients having cerebrovascular diseases. Another disadvantage is that the injection of the contrast medium can lead to changes to the natural pressure ratios and therefore to differing results compared with the actual situation. It is also only possible to represent vessels up to a specific minimum size. Therefore the method provides no information on the actual blood flow of the tissue (perfusion), because it is not possible to detect the capillary vessels responsible for this.

A possible alternative is provided by non-invasive methods, in which the arteries supplying the brain and the blood flowing through the brain regions is itself used as an intrinsic contrast medium. This method is known as arterial spin labelling (ASL).

For the determination of the cerebral blood circulation a labelling experiment and a control experiment are performed for this purpose. In the labelling experiment the magnetization of the blood in the arteries supplying blood and oxygen to the brain is inverted with suitable pulse sequences. In a phase following onto labelling the blood flowing into the brain is detected with an imaging method (e.g. echo planar imaging or EPI). However, in the control experiment pulse sequences are used which do not change the magnetization of the blood in the ideal case. It is a prerequisite that the pulses used in the control experiment have the same saturation effect as the pulses used during labelling. This ensures that the images of the labelling and control experiments, with the exception of the different magnetization state of the blood, are identical and the cerebral perfusion territories can be rendered visible by subtraction of the in each case associated images.

As a function of the type of pulses used, arterial spin labelling is subdivided into two methods. In the pulsed ASL method (PASL) short inversion pulses are used, which invert the magnetization state of the blood in a thick coating proximal to the area under investigation and the labelled blood flows into the tissue after inversion has taken place. However, in the continuous ASL method (CASL), continuous RF pulses with a length of approximately 2 seconds are used and give rise to an adiabatic inversion of the magnetization state of the blood flowing into the tissue. A frequently used CASL method with an amplitude-modulated control experiment is described by DC ALSOP and JA DETRE ("Multisection cerebral blood flow MR imaging with continuous arterial spin labelling" (1998) Radiology 208 (2): 410-6).

The disadvantage of the conventional ASL method is that the representation of territories associated with a single blood vessel is only possible in a few cases. The spatial arrangement of the blood vessel system and the spatial resolution achievable with the known method consequently essentially always lead to a representation of several territories which can be tracked back to several blood vessels.

Therefore the problem of the invention is to provide a method for MRT representation of a blood vessel and/or the territory supplied by the blood vessel by labelling the blood guided by the blood vessel by means of continuous spin labelling, which permits a more precise labelling of a single artery and therefore a representation of a perfusion territory supplied by a single artery.

The problem is solved by a method for MRT representation of a blood vessel and/or the territory supplied by the blood vessel by labelling the blood guided by the blood vessel using continuous spin labelling in a specific labelling plane, which is varied in such a way that a specific position of the blood vessel remains in the labelling plane.

Thus, the method according to the invention makes use of labelling for MRT representation of a blood vessel (A) and/or the territory supplied by the blood vessel (A) by means of continuous spin labelling in a specific labelling plane (E), the position of the labelling plane (E) being varied provided that a specific position of the blood vessel (A) remains in the labelling plane (E). This can mean e.g. a periodic variation of the labelling plane (E) and/or a stepwise variation of the labelling plane (E) during labelling. However, the position of the labelling plane can also be varied in a non-periodic manner.

The method makes it possible to represent one blood vessel and/or the territory supplied by said blood vessel. This includes both the labelled blood vessel and the vascular tree distally following on to said blood vessel. As a result it is possible to produce angiograms of vessels or vascular trees. Representation also takes place of the blood flow of the tissue supplied by the labelled vessel, i.e. the vessel perfusion territory. Apart from the exemplified use for the representation of cerebral perfusion territories, the method can also be used for the representation of vessels, vascular trees and/or perfusion territories in random other organs, such as e.g. the kidneys, heart, lungs, prostate or muscles of the locomotor system. The method can also contribute to the clarification of the significance of a specific blood vessel for the supply of pathologies, such as e.g. fistulas, aneurysms or tumours. The method can be used both for labelling arterial and venous blood.

By varying the position of the labelling plane in the manner defined in claim 1 three effects are simultaneously obtained. Firstly the influencing of the magnetization during the labelling experiment and control experiment in the vicinity of the stationary point of the labelling plane, which coincides with the blood vessel to be labelled, is virtually identical with the influencing of magnetization obtained in the case of a stationary labelling plane. This means that the labelling in this area is similarly effective to a non-selective labelling of the blood flowing through a stationary plane.

Secondly magnetization saturation occurs at a distance from the stationary point of the plane, both in the labelling and in the control experiment. This effect is based on a pseudorandom distribution of the magnetization of individual spin groups, which repeatedly pass through the moving plane.

Thirdly the influence of the pulse sequences used during the labelling and control experiments on the magnetization in the vicinity of the imaging volume is identical in both the labelling and the control experiment. As a result the so-called off-resonance effects are compensated.

According to a development the labelling plane position is periodically varied. This offers the advantage that the pulse sequence for the labelling and control experiments is also periodic and the non-rotational or gradient fields to be time-varied and the amplitude and frequency modulation of the RF pulses only have to be calculated for one period or cycle. The sequence calculated for one cycle can then be correspondingly repeated.

According to a development the labelling plane position is varied stepwise. This makes it possible to obtain a particularly simple pulse sequence, which does not require the use of fields varying in time-continuous manner. Instead the gradients and RF fields are switched stepwise. For example, the size of the steps can be kept so small that an approximately continuous variation of the labelling plane position is obtained. Usable results are also obtainable when using larger steps.

Preferably by the choice of a labelling plane (E) inclined with an inclination angle θ to the longitudinal axis of the blood vessel (A) and the rotation of the inclined labelling plane (E) about the blood vessel (A) as the longitudinal axis, preferably with a constant inclination angle, but also with varying inclination angles, a representation can be obtained.

The size of the inclination angle and the frequency of the rotational motion is freely selectable within wide ranges. The inclination angle θ can e.g. assume values between 1 and 60°, preferably values between 5 and 25°. Values in the range 5 to 1000 Hz, preferably 40 to 300 Hz can e.g. be used for the rotational motion frequency. A suitable combination of both parameters is vital for a successful selective labelling. A part is also played here by matching to the blood flow rate, which can vary as a function of the particular use.

The invention is described in greater detail hereinafter relative to a preferred embodiment and the attached drawings, wherein show:

FIG. 1 A diagrammatic representation of the spatial relationships between the labelling plane and the artery to be labelled.

Figure 2:
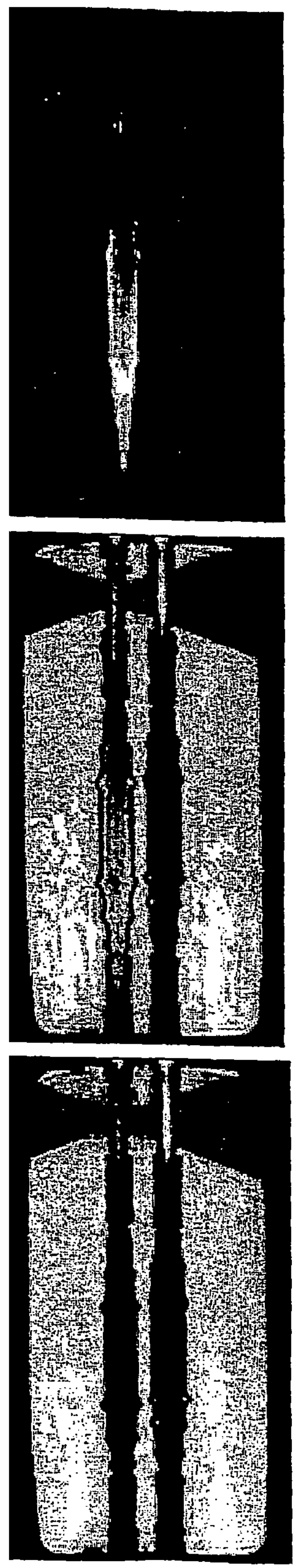

FIG. 2 A MRT representation of a labelling experiment and a control experiment and the subtraction representation of both experiments performed on a phantom.

Figure 3:
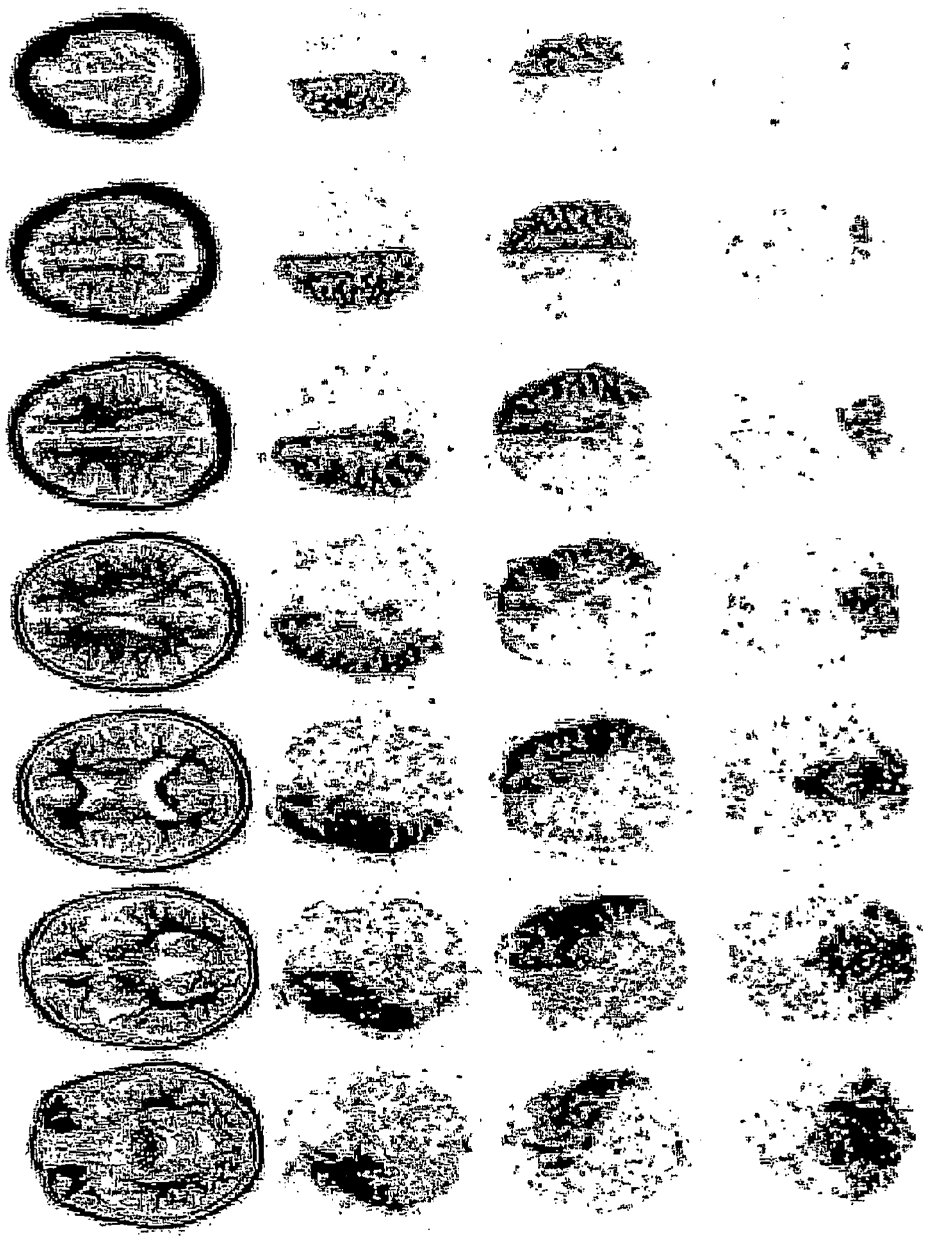

FIG. 3 An inverted representation of a MRT representation of cerebral perfusion territories performed with the method according to the invention.

FIG. 1 shows the spatial circumstances between the labelling plane E and the blood vessel A guiding the blood to be labelled for representing a blood vessel and/or a territory supplied by a blood vessel. The blood vessel can be of any type. However, normally the blood vessel is an artery and in a preferred application in neuroradiology the territory to be represented is a cerebral perfusion territory supplied by an artery.

The labelling plane E is varied in such a way that a specific point of the blood vessel A remains in the labelling plane E. The variation of the labelling plane E can consist of tilting, inclining or rotating about a position of the blood vessel, preferably a point, but at the most a limited portion, the position of the blood vessel remaining in the labelling plane.

In the preferred embodiment shown in FIG. 1 the labelling plane E is so positioned relative to the longitudinal axis of blood vessel A, that the labelling plane E is inclined in a particularly preferred, constant angle θ relative to the longitudinal axis of blood vessel A. For the labelling of the blood flowing through blood vessel A, the labelling plane E rotates with a frequency $f_{rot}$ about the blood vessel A as the longitudinal axis.

The frequency of the labelling RF pulse is controlled in such a way that it always corresponds to the resonant frequency at the position on the blood vessel A where the blood is labelled. The labelling plane E is varied in such a way that a specific position of the blood vessel always remains in the labelling plane E.

FIG. 2 shows the results of a labelling experiment (a) and a control experiment (b) performed on a phantom with the inventive method. The dark cones shown in FIGS. 2*a* and 2*b* are artifacts appearing at a point where the rotating labelling plane intersects the image plane. FIG. 2*c* shows the subtraction image from the labelling and control experiments. The phantom consisted of two parallel tubes with an internal diameter of 6 mm embedded with a spacing of 20 mm in agarose gel. Each tube was connected to a glass tube clip having at its ends a diameter of 6 mm, widening to approximately 12 mm towards the centre. As a result the flow rate of the water used in the thinner portions where labelling was carried out could be adjusted to physiological values, whereas the rate in the thicker portions was significantly reduced and consequently magnetization measurement in these areas was simplified. The parameters used for this experiment were: $f_{rot}$=80 Hz; θ=20° and v=35 cm/s.

As a result of the relative movement of the labelling plane and the blood vessel to be labelled in a distance d from the blood vessel to be labelled, the labelling mechanism becomes ineffective. Instead there is a saturation of the magnetization of the flowing blood at the position of the blood vessel not to be labelled. This applies both for the labelling and for the control experiment, so that the blood is not visible in the subtraction image.

FIG. 3 shows an inverted representation of a MRT representation of cerebral perfusion territories performed with the method according to the invention. For assigning the sectional planes, the upper row contains anatomical views as a reference. The second row contains views of the perfusion territories for the right internal carotid artery. The third row contains views of the perfusion territories for the left internal carotid artery and the fourth row views of the perfusion territories for the basilar artery. Each scan lasted 5 minutes and seven 9 mm thick coatings were produced with a spin-echo echo planar imaging method (SE-EP1).

Using the example of cerebral perfusion territories, FIG. 3 shows that the method according to the invention permits a selective labelling of individual, spatially closely juxtaposed blood vessels. Using this method it is e.g. possible to separately represent the perfusion territories of the left and right internal carotid arteries and the basilar artery.

The invention claimed is:

1. A method for continuous arterial spin labeling of a blood vessel or territories supplied by the blood vessel comprising:

labelling blood guided by the blood vessel through continuous arterial spin labelling in a specific labeling plane; and varying a position of the labelling plane, provided that a specific position of the blood vessel remains in the labelling plane.

2. The method according to claim 1, characterized by a periodic variation of the position of the labelling plane during labelling.

3. The method according to claim 2, further comprising: stepwise varying the position of the labelling plane during labelling.

4. The method according to claim 1, further comprising: stepwise varying the position of the labelling plane during labelling.

5. The method according to claim 1, further comprising: choosing a labeling plane inclined by an inclination angle θ to a longitudinal axis of the blood vessel and rotating the inclined labelling plane about the blood vessel as the longitudinal axis.

6. The method according to claim 5, wherein the inclination angle θ is maintained constant.

7. The method according to claim 1, carried out in a cerebral perfusion territory.

8. A continuous arterial spin labeling method for magnetic resonance tomography imaging of a blood vessel and/or a territory supplied by the blood vessel comprising:

adiabatically inverting a magnetization of the blood carried in the blood vessel when the blood is flowing through a marking plane by continuous RF pulses during a marking operation; and varying a position of the marking plane during adiabatic inversion with a proviso that a certain location of the blood vessel remains in the marking plane.

9. The method according to claim 8, characterized by periodically varying the position of the marking plane during the adiabatic inversion.

10. The method according to claim 9, characterized by stepwise varying the position of the marking plane during the adiabatic inversion.

11. The method according to claim 10, characterized by selecting a marking plane inclined at an angle θ of inclination relative to a longitudinal axis of the blood vessel and rotating the inclined marking plane about the blood vessel as the longitudinal axis during the adiabatic inversion.

12. The method according to claim 9, characterized by selecting a marking plane inclined at an angle θ of inclination relative to a longitudinal axis of the blood vessel and rotating the inclined marking plane about the blood vessel as the longitudinal axis during the adiabatic inversion.

13. The method according to claim 9, characterized in that the territory is a cerebral perfusion territory.

14. The method according to claim 8, characterized by stepwise varying the position of the marking plane during the adiabatic inversion.

15. The method according to claim 14, characterized by selecting a marking plane inclined at an angle θ of inclination relative to a longitudinal axis of the blood vessel and rotating the inclined marking plane about the blood vessel as the longitudinal axis during the adiabatic inversion.

16. The method according to claim 8, characterized by selecting a marking plane inclined at an angle θ of inclination relative to a longitudinal axis of the blood vessel and rotating the inclined marking plane about the blood vessel as the longitudinal axis during the adiabatic inversion.

17. The method according to claim 16, characterized in that the angle θ of inclination is constant during the adiabatic inversion.

18. The method according to claim 16, characterized in that the territory is a cerebral perfusion territory.

19. The method according to claim 8, characterized in that the territory is a cerebral perfusion territory.

* * * * *